United States Patent [19]
Khouri

[11] Patent Number: 6,083,912
[45] Date of Patent: *Jul. 4, 2000

[54] METHOD FOR SOFT TISSUE AUGMENTATION

[75] Inventor: Roger K. Khouri, 2 Kingsbury Pl., St. Louis, Mo. 63112

[73] Assignee: Roger K. Khouri, Key Biscayne, Fla.

[ * ] Notice: This patent issued on a continued prosecution application filed under 37 CFR 1.53(d), and is subject to the twenty year patent term provisions of 35 U.S.C. 154(a)(2).

[21] Appl. No.: 08/432,517

[22] Filed: May 1, 1995

[51] Int. Cl.$^7$ .......................... A61K 38/16; A61K 38/18

[52] U.S. Cl. .............................. 514/12; 514/21; 530/399; 424/422

[58] Field of Search ..................................... 424/426, 422; 514/12, 21; 530/399

[56] References Cited

U.S. PATENT DOCUMENTS

| | | | |
|---|---|---|---|
| 4,774,091 | 9/1988 | Yamahira et al. | 424/426 |
| 5,273,900 | 12/1993 | Boyce | 435/240 |
| 5,308,889 | 5/1994 | Rhee et al. | 523/113 |
| 5,723,115 | 3/1998 | Serrero | 424/85.1 |

OTHER PUBLICATIONS

Zezulak, K.M. et al. Science, 233 (4763), 551–553, Sep. 1986.
Butterwith, S.C. et al J. Endocrinol, 134(2), 163–168, Feb. 1992.
Campbell et al., Paradoxical lipodystrophic changes due to conventional bovine and highly purified porcine/bovine insulins, *Postgraduate Medical Journal* 60:439–441 (1984).
Lorenzo et al., IGF–I Is a Mitogen Involved in Differentiation–related Gene Expression in Fetal Rat Brown Adipocytes, *J. of Cell Biology*, 123, 6:1567–1575 (1993).
Breast Augmentation by Ilana Harman–Boehm, The Diabetes Care, vol. 12, No. 8, pp. 597–598, 1989.

The Influence of Dexamethasone on the Regrowth of Surgically Removed Fat by Angel et al., Ann Plast Surg 17:134–40 (1986).

In Vivo Metabolic Action of Insulin–Like Growth Factor I in Adult Rats, by Schmitz et al., Diabetologia, vol. 34, pp. 144–149, 1991.

Studies of Acute Effects of Insulin–Like Growth Factor I and II in Human Fat Cells, by Bolinder et al., Journal of Clinical Endocrinology and Metabolism, vol. 65, pp. 732–737, 1987.

How Distinct are the Insulin and Insulin–Like Growth Factor I Signalling Systems? by Adamo et al., BioFactors, vol. 3, No. 3, pp. 151–157, 1992.

Actions of Insulin–Like Growth Factors, by Froesch et al., Ann. Rev. Physiol., vol. 47, pp. 443–467, 1985.

Insulin–Like Growth Factor–I Is an Essential Regulator of the Differentiation of 3T3–L1 Adipocytes, by Smith et al., The Journal of Biol. Chem., vol. 263, No. 19, pp. 9402–9408, 1988.

*Primary Examiner*—Michael P. Woodward
*Assistant Examiner*—Michael Borin
*Attorney, Agent, or Firm*—Howell & Haferkamp, L.C.

[57] ABSTRACT

Disclosed herein is a method for augmentation of soft tissue in an individual comprising administering percutaneously to the individual at a site for soft-tissue augmentation, a growth factor in an amount effective in eliciting a stable, localized growth of autologous vascularized adipose tissue. Applicable growth factors include IGF-I and IGF-II. The method is useful in treating soft tissue contour defects.

13 Claims, 2 Drawing Sheets

METHOD FOR SOFT TISSUE AUGMENTATION

BACKGROUND OF THE INVENTION (1) Field of the Invention

This invention relates generally to the field of plastic and reconstructive surgery and, more particularly, to methods for soft tissue augmentation using growth factors.

(2) Description of the Related Art

Many procedures in plastic and reconstructive surgery involve the correction of soft tissue contour defects. Patients with conditions like hemifacial microsomia, Romberg's disease, traumatic injuries, cancer resection surgeries, and depressed scars as seen following severe acne, chicken pox or smallpox all suffer from substantial soft tissue contour defects. In addition, the desire to enlarge a soft tissue site might produce a need for augmentation such as breast or penile augmentation. Such conditions requiring contour correction or enlargement are usually reconstructed with flaps of autogenous tissue, with alloplastic implants or with prosthetic implants. Flap reconstruction often involves extensive surgical procedures that can lead to significant donor site morbidity and scarring. Furthermore, implants have the disadvantage that they can migrate, extrude, become infected, or cause painful and deforming capsular contractures.

Tissue augmentation with injections of autologous fat is an approach that avoids prosthetic implants or a surgical procedure. Nevertheless, because the injected fat is avascular, it resorbs over time. It would, therefore, be desirable to have a method for augmenting soft tissues to generate stable, localized deposits of vascularized adipose tissues and it would further be desirable if the method were nonsurgical.

Previous studies have demonstrated that substances such as dexamethasone can be administered systemically to influence the growth of regional fat deposits. Chronic, systemic administration of dexamethasone resulted in an increase in fat deposits in certain regions and this increase was due to both an increase in cell size, i.e. hypertrophy, and an increase in cell number, i.e. hyperplasia (Angel et al. 134–140, 1982). In man, systemic administration of adrenal corticosteroids are known to produce characteristic and undesirable changes in fat distribution. These changes are considered a detrimental side effect and typically include deformities referred to as "moon facies" and "buffalo humps". Paradoxically, local subcutaneous administration of steroids is known to cause fat atrophy. Thus, steroids have not been shown to produce a localized increase in fat growth when administered at a particular target site.

One group of substances known to be growth factors are the insulin-like growth factor family of peptides which include insulin, Insulin-Like Growth Factor-I (IGF-I) and Insulin-Like Growth Factor-II (IGF-II). (Froesch et al., *Ann Rev Physiol* 47:443–67, 1985 which is incorporated by reference). Insulin is known to be a lipogenic growth factor. Because of this property, the use of insulin could provide a possible approach for stable soft tissue augmentation, however, insulin is also capable of producing a potent hypoglycemic effect. On the other hand, IGF-I, is another member of the insulin-like growth factor family of peptides, similar to insulin in structure and function. IGF-I produces lipogenesis in epididymal fat pads and hypoglycemia in rats and inhibition of lipolysis in human fat cells apparently mediated through insulin receptors although IGF-I was less potent than insulin in these actions (Schmitz et al. *Diabetologia* 34:144–149, 1991; Bolinder et al., *J Clin Endrocrinol Metabol* 65:732–737 which are incorporated by reference). In contrast to these actions mediated through the insulin receptor, IGF-I can also act to stimulate growth and development through specific high-affinity type I IGF receptors that are distinct from insulin receptors mediating lipogenesis. (Adamo et al., *BioFactors* 3:151–157, 1992; Frosch et al., 1985 which are incorporated by reference). An action of IGF-I at these receptors might be expected to produce a stimulation of growth without eliciting a hypoglycemic effect. IGF-II and Insulin, at high concentrations, are also known to bind to IGF-I receptors. Furthermore, IGF-II can also stimulate growth although this substance is about one-third as potent as IGF-I in stimulating DNA synthesis in human fibroblasts. (Id.). Nevertheless, none of the peptides from the insulin-like growth factor family of peptides have been utilized heretofore for promoting localized growth of soft tissues in an individual.

SUMMARY OF THE INVENTION

Applicant has succeeded in devising a novel nonsurgical method for soft-tissue augmentation. The method comprises administering percutaneously at a desired site for soft-tissue augmentation, a growth factor in an amount effective in eliciting a stable, localized deposit of vascularized tissue, in a physiologically acceptable carrier.

Growth factors that can be used include peptides from the insulin-like growth factor family of peptides and derivatives thereof. Thus, one embodiment of the present invention is the administration of a peptide from the insulin-like growth factor family of peptides, in particular, IGF-I, IGF-II or insulin. The localized administration of IGF-I, IGF-II or insulin will elicit a stimulation of growth at the site of administration to produce vascularized adipose tissue in which the growth comprises hyperplasia of adipocytes.

Among the several advantages found to be achieved by the present invention, therefore, may be noted the provision of a nonsurgical method for soft tissue augmentation; the provision of a method for producing a localized deposit of vascularized soft tissue that is stable and not resorbed over time; the provision of a method for producing a deposit of soft tissue that does not migrate, extrude, become infected or cause capsular contractures.

DESCRIPTION OF PREFERRED EMBODIMENTS

Figure 1A:
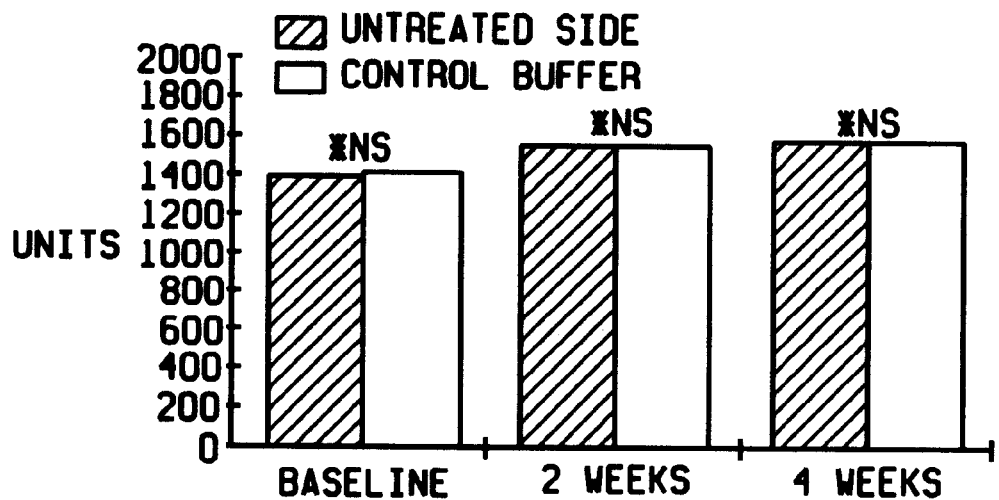
FIG. 1 is a bar graph illustrating fat pad volumes in untreated and treated sides measured by magnetic resonance imaging (MRI) at baseline, 2 weeks and 4 weeks into the study (A) in control animals receiving buffer and (B) in animals receiving 1 mg of recombinant human IGF-I every five days until day fifteen for a total of four injections.

In accordance with the present invention, it has been discovered that percutaneous administration of a growth factor produces a localized soft-tissue augmentation comprising a growth of adipocytes. Surprisingly, the growth was stable and not resorbed over time and provided a localized deposit of tissue. The present invention, thus, provides the plastic and reconstructive surgeon with a new nonsurgical method for generating a well-defined deposit of vascularized autologous tissue and thereby obviates the need for extensive surgical repair of soft tissue contour defects.

The growth factor can be any growth factor known in the art that is able to produce a localized deposit of tissue upon administration percutaneously to a site for soft tissue augmentation. Preferred growth factors are family members of the insulin-like growth factor family of peptides, including IGF-I and IGF-II.

The insulin-like growth factor family of peptides applicable in the present invention can be obtained from human or animal sources (for example see Humbel, *Eur J Biochem* 190:445–462, 1990 which is incorporated by reference). Furthermore, the peptides from the insulin-like growth factor family can be produced by any method known in art, for example by isolation from serum or by production using recombinant DNA techniques.

Preferred as growth factors are human peptides from the insulin-like growth factor family made by recombinant DNA technology. Human IGF-I has been characterized in the art as to the sequence of amino acids which is known to be the following:
G P E T L C G A E L V D A L Q F V C G D R G F Y-F N K P T G Y G S S S R R A P Q T G I V D E C C F R S C D L R R L EMY-CAPLKPAKSA (SEQ ID NO: 1). (Rinderknecht et al., *J Biol Chem* 253:2769–2776, 1978; Jansen et al., *Nature* 306:609–611, 1983 which are incorporated by reference). The cysteines in positions 6 and 48, positions 18 and 61, and positions 47 and 52 form disulfide bonds. Human IFG-II is also well known in the art to have the sequence as follows: A Y R P S E T L C G G E L V D T L Q F V C G D R G F Y F - S R P A S R V S R R S R G I V E E C C F R S C D L A L L E TYCAT-PAKSE (SEQ ID NO: 2). (Rinderknecht et al., supra, 1978; Jansen et al., *FEBS Lett* 179:243–246, 1985; Bell et al., *Nature* 310:775–777, 1984 which are incorporated by reference). The cysteines in positions 9 and 47, positions 21 and 60, and positions 46 and 51 form disulfide bonds. Most preferred as a growth factor is recombinant human IGF-I.

Derivatives can also be made that produce soft tissue augmentation according to the present invention. Peptide derivatives are polypeptides that have sufficient sequence homology with IGF-I or IGF-II to exhibit the property of producing an increase in growth of adipose tissue at a local site of administration. Such peptides can be produced by any standard synthetic procedure known in the art. Non-peptide derivatives that are capable eliciting the growth stimulating effects of the insulin-like growth factor peptides can also be made based on the structural features of the critical amino acid sequence of the peptides. Techniques for making peptide mimetics are well known in the art. (See for example, Navia and Peattie, *Trends Pharm Sci* 14:189–195, 1993; Olson et al, *J Med Chem* 36:3039–3049 which are incorporated by reference).

Administration of the growth factor is at the local site at which soft tissue augmentation is desired by any suitable method of administration known in the art. For example, administration can be by implantation or injection of the growth factor in an pharmaceutically acceptable carrier. Alternatively, administration can be by percutaneous absorption using any carrier system suitable for percutaneous absorption such as creams, ointments, emollients and the like. The preferred method of administration is by injection percutaneously at the site for soft tissue augmentation.

Local administration of insulin-like growth factors and derivatives thereof at the site for soft tissue augmentation increases growth of adipocytes at the site of injection. The growth results in an increase in weight of the fatty tissue at the site of injection. The generated fat is normal on pathologic examination both in gross and microscopic appearance. The growth-factor generated fat cells are not larger than cells in comparable untreated fat tissue which indicates that growth is due to hyperplasia, i.e. an increase in the number of cells.

The local increase in growth is selective in that no systemic effects are produced. Although it is not intended that the present invention be limited by a particular mechanism of action, the selectivity produced by local injection might be explained by several factors. First, the local injection would be expected to produce a higher concentration of the peptide at the site of injection compared to systemic concentrations of the drug. A greater effect at the site of injection might also be facilitated by the presence of IGF-I and IGF-II binding proteins in the serum could effectively decrease serum levels of growth factors, IGF-I and IGF-II. Second, a growth factor such as IGF-I might act at high affinity IGF-I receptors rather than at insulin receptors to stimulate growth in the adipose cells. IGF-I receptors have been shown to be present in the fat cells although human adipocytes express far more insulin receptors that IGF-I receptors (Adamo et al., supra). Finally, it is possible that a growth factor such as IGF-I could produce an adipocyte growth by eliciting a differentiation of preadipocytes, an effect shown to be mediated by IGF-I receptors in rat preadipocytes (Smith et al., *J Biol Chem* 263:9402–9408, 1987 which is incorporated by reference).

The dosages required will vary with the particular growth factor used and need only be an amount effective in eliciting a stable, localized growth of autologous vascularized tissue. Effective amounts for IGF-I and IGF-II are based upon the well known activities of these substances in in vivo and in vitro models and are easily determinable by routine experimentation. Doses of IGF-I are typically from about 0.025 to about 5.0 mg and doses of IGF-II are typically from about 0.050 to about 10.0 mg.

It will be understood that the amount of the growth factor actually administered will be determined by a physician, in the light of the relevant circumstances including the condition or conditions causing the contour defect, the choice of composition and growth factor to be administered, the age, weight, and response of the individual patient, the severity of the patient's soft tissue contour defects, and the method of administration, and, therefore, the above dosage ranges are not intended to limit the scope of the invention in any way.

The growth factor is administered in a pharmaceutically acceptable carrier. The pharmaceutical carrier or excipient can be any liquid or solid in which the growth factor is suspended or dissolved so long as the carrier or excipient is non-toxic to the individual to which it is administered. Suitable pharmaceutical carriers are known in the art, and, for example, include liquid carriers, such as normal saline and other non-toxic salts at or near physiological concentrations. Adjuvants may be added to enhance the growth stimulating effect if desired. Suitable pharmaceutical carriers and adjuvants and the preparation of dosage forms are described in, for example, Remington's Pharmaceutical Sciences 17th Edition, (Gennaro, Ed., Mack Publishing Co., Easton, Pa., 1985 which is incorporated by reference).

Single administration or repeated administration of the growth factor may be used in achieving the desired growth of tissue. When repeated administration is desired, a given injection of the growth factor would be followed by a repeated injection of the growth factor some time later. The repeated injection would be at a time determined by routine experimentation to increase the effect produced by the prior dose. Typically a repeated dose would be given from about one to about five days after the prior dose.

The ability to augment existing tissues without surgery has many potential applications in the correction of soft tissue contour defects. Patients having hemifacial microsomia, Romberg's disease, traumatic injuries, cancer, or depressed scars from severe acne, chicken pox or smallpox or patients desiring breast or penile augmentation could be spared the risks and complications of extensive surgeries and prosthetic implants if contour defect reconstruction can be achieved nonsurgically with percutaneous injections of lipogenic growth factors.

The above disclosure generally describes the present invention. A more complete understanding can be obtained by reference to the following specific example which is provided herein for purposes of illustration only and is not intended to be limiting unless otherwise specified.

Example of the Preferred Embodiment

The following example illustrates the generating of a stable fat pad by local injection of IGF-I in rats.

These experiments utilized the groin fat pad of the rat, which is a well-defined island of fat supplied by the superficial epigastric artery, a branch of the femoral artery. Male Lewis rats were used weighing between 100 and 125 grams. The animals had free access to water and a standard rat diet. Recombinant human IGF-I was supplied by Amgen, Inc. Thousand Oaks, Calif. Ten mg of the growth factor was dissolved in 10 ml of 0.1M acetic acid (2.0 mg/ml) and delivered to the animals via disposable syringes with 30-gauge needles at a concentration of 1 mg/ml and a dose of 1 mg. Control buffer was 0.1M acetic acid without growth factor and was administered in the same way. In a blinded, randomized fashion, each of eight rats was injected with either IGF-I or control buffer, with n=4 in each group. While the animals were being restrained gently in a large cloth glove, the injections were given subcutaneously into the right groin fat pad of each animal, with the uninjected left side serving as a systemic control.

The time course of the study was such that injections were given every five days until day fifteen, with each animal receiving a total of four injections. At baseline, two weeks, and four weeks into the study, the animals were anesthetized with a subcutaneous injection of ketamine and procaine given in the interscapular region and studied with T1-weighted Magnetic Resonance Imaging (MRI) to non-invasively follow the progression of fat generation. Three dimensional volumetric reconstruction of the images was used to measure the amount of generated fat. Also four weeks into the study, two weeks after the last injection, the rats were anesthetized and shaved and depilated to evaluate the gross appearance of their groins On day 35, three weeks after the last injection, the animals were sacrificed with an overdose of pentobarbital and the groin fat pads were dissected out from the inferior margin of the ribs superiorly to the inguinal region inferiorly and from the ventral midline medially to the midaxillary line laterally. The specimens were carefully trimmed of connective tissue, weighed and fixed in buffered formaldehyde solution. The tissues were then processed, cut into sections, stained with Hematoxylin and Eosine and O-Red-O stains for fat, and examined microscopically.

Paired student's t-test was used to analyze statistical significance of differences in both weights and volumes between the IGF-I treated or control buffer treated fat pads compared to the untreated contralateral fat pads of the same animals.

Figure 1B:
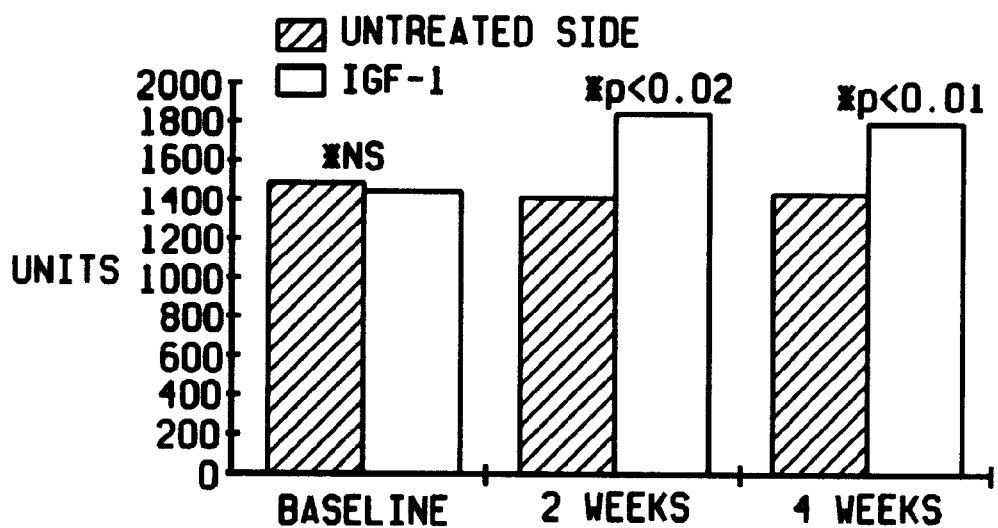

MRI studies in the control group showed no significant difference in fat pad volume between the control buffer injected side and the uninjected contralateral side of the same animals at two weeks and four weeks (FIG. 1). In contrast, in the experimental group, the IGF-I treated fat pads were an average of 21% larger volume (p<0.01) compared to the untreated contralateral side of the same animals at both two weeks and four weeks into the study (FIG. 1).

Also four weeks into the study, the animals were shaved and depilated to evaluate the gross appearance of their groins). There was no visible soft tissue augmentation in any of the fat pads of the animals receiving control buffer. In each of the experimental animals, however, there was a pliable, mobile soft tissue bulge that was readily visible and on the IGF-I treated side only. There were no such bulges on the untreated contralateral sides of the experimental animals.

At week five the animals were sacrificed and their groin fat pads were removed, fixed, and weighed. When the skin was reflected and the fat was separated from the underlying muscles, there was no noticeable difference in size between the control buffer treated and untreated fat pads in the control animals. In the experimental animals, the IGF-I treated fat pads were noticeably enlarged compared to the untreated contralateral fat pads.

Figure 2A:
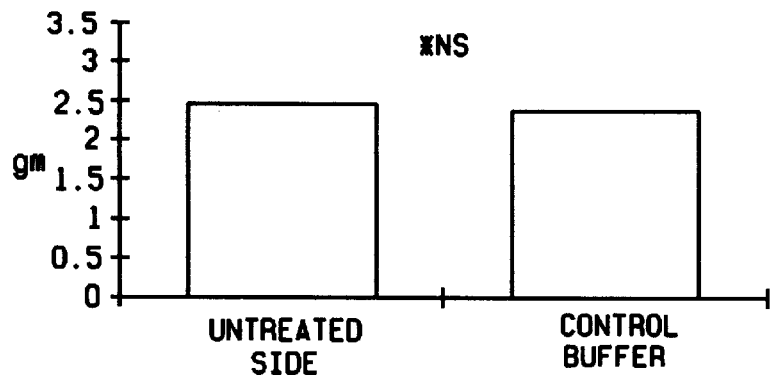
FIG. 2 is a bar graph illustrating the wet weights of fat pads in (A) control animals and (B) in experimental animals receiving 1 mg of recombinant human IGF-I every five days until day fifteen for a total of four injections.
Figure 2B:
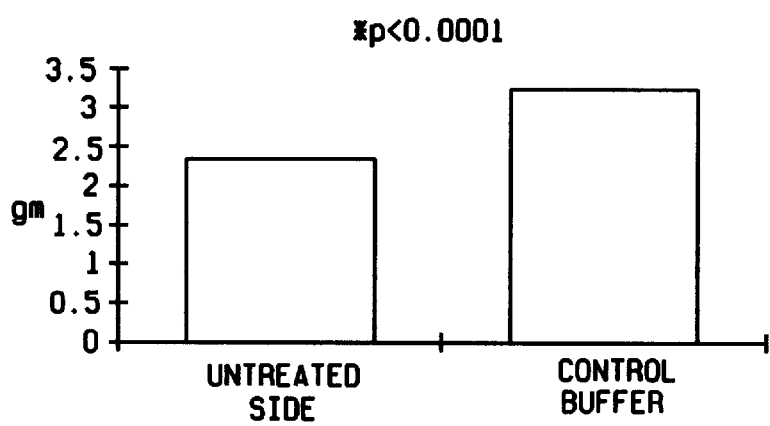
Figure 3:
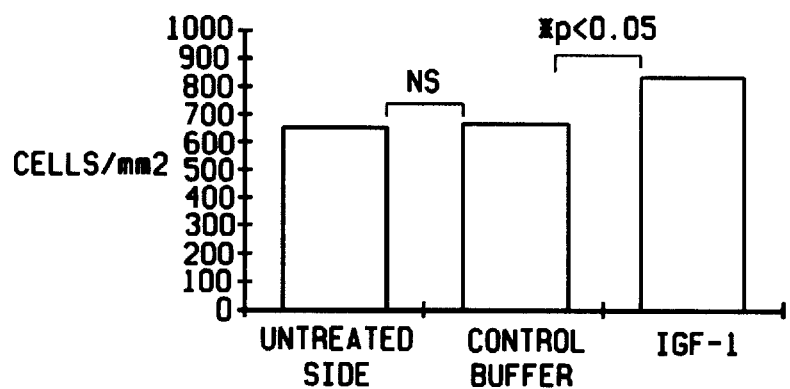
FIG. 3 is a bar graph illustrating the increase in the fat cell count in fat pads from animals receiving 1 mg of recombinant human IGF-I every five days until day fifteen for a total of four injections.

When the fat pads were weighed, the untreated fat pads of the control animals had an average weight of 2.5 grams, wet weight. There was no significant difference between these and the control buffer treated fat pads, which had an average weight of 2.45 grams (FIG. 2). In the experimental group, the untreated fat pads had an average weight of 2.3 grams, while the IGF-I treated fat pads had an average weight of 3.2 grams (p<0.0001) (FIG. 2). The fat cell count was also increased in IGF-I treated fat pads compared to fat pads treated with buffer (FIG. 3).

The specimens obtained at harvest showed no evidence of necrosis, calcification, or dysplastic changes. The generated fat appeared both grossly and microscopically normal. Histologically, the IGF-I generated fat was similar in appearance to both the control buffer treated fat and the untreated fat of both the control and experimental animals.

Because the adipocytes of the IGF-I generated fat were not larger compared to cells from the control buffer treated or the untreated fat pads, the mechanism of fat growth was likely to be hyperplasia and not hypertrophy. The IGF-I generated adipocytes did not appear smaller, as might be expected of newly divided cells, but the harvest occurred three weeks after the last injection, giving the newly divided adipocytes time to fill with fat and enlarge to the size of their predecessors. In the three weeks between the last injection and the harvest, there was no evidence of regression of the IGF-I generated fat pads detected by MRI.

Although serum glucose was not measured during this study, there was no evidence that the animals were hypoglycemic. There was no noticeable size discrepancy between the experimental and control animals. Furthermore, subcutaneous injections of the IGF-I directly into the groin fat pads give the free growth factor the opportunity to exert its effect in the local tissues before being absorbed into the animals' systemic circulation, where the IGF-I is highly protein bound and therefore much less active systemically.

These results demonstrate that nonsurgical tissue augmentation can be achieved using percutaneous injections of IGF-I. This is the first study to applicant's knowledge that shows the generation of localized stable tissue augmentation by subcutaneous injections of a lipogenic growth factor at a specific desired site.

In view of the above, it will be seen that the several objects of the invention are achieved and other advantageous results attained.

As various changes could be made in the above constructions without departing from the scope of the invention, it is intended that all matter contained in the above description shall be interpreted as illustrative and not in a limiting sense.

What is claimed is:

1. A method for augmentation of soft tissue comprising eliciting a localized hyperplasia of adipocytes by percutaneous administration to the soft tissue, a growth factor other than insulin, in a pharmaceutically acceptable carrier.

2. The method of claim 1 wherein the growth factor comprises a peptide from the insulin-like growth factor family of peptides.

3. The method of claim 2 wherein the peptide is IGF-I.

4. The method of claim 3 wherein IGF-I is administered by percutaneous injection.

5. The method of claim 3 wherein IGF-I is administered by percutaneous absorption from topical application.

6. The method of claim 3 wherein the soft-tissue augmentation is correcting for a contour defect resulting from hemifacial microsomia, Romberg's disease, traumatic injury, cancer or a depressed scar from severe acne, chicken pox or smallpox.

7. The method of claim 3 wherein the soft-tissue augmentation is penile augmentation.

8. The method of claim 2 wherein the peptide is IGF-II.

9. The method of claim 8 wherein IGF-II is administered by percutaneous injection.

10. The method of claim 8 wherein IGF-II is administered by percutaneous absorption from topical application.

11. The method of claim 8 wherein the soft-tissue augmentation site is correcting for a contour defect resulting from hemifacial microsomia, Romberg's disease, traumatic injury, cancer or a depressed scar from severe acne, chicken pox or smallpox.

12. The method of claim 8 wherein the soft-tissue augmentation is penile augmentation.

13. The method of claim 2 wherein the percutaneous administration of the growth factor other than insulin is repeated at least once.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
       (A) LENGTH: 70 amino acids
       (B) TYPE: amino acid
       (D) TOPOLOGY: linear (ii) MOLECULE TYPE: protein (iii) HYPOTHETICAL: NO (ix) FEATURE:
       (A) NAME/KEY: Disulfide-bond
       (B) LOCATION: 6..48
       (D) OTHER INFORMATION: /note= "Disulfide bond between two
           cysteines."

(ix) FEATURE:
       (A) NAME/KEY: Disulfide-bond
       (B) LOCATION: 18..61
       (D) OTHER INFORMATION: /note= "Disulfide bond between two
           cysteines."

(ix) FEATURE:
       (A) NAME/KEY: Disulfide-bond
       (B) LOCATION: 47..52
       (D) OTHER INFORMATION: /note= "Disulfide bond between two
           cysteines."

(xi) SEQUENCE DESCRIPTION: SEQ ID NO:1:

Gly Pro Glu Thr Leu Cys Gly Ala Glu Leu Val Asp Ala Leu Gln Phe
1               5                   10                  15

Val Cys Gly Asp Arg Gly Phe Tyr Phe Asn Lys Pro Thr Gly Tyr Gly
                20                  25                  30

Ser Ser Ser Arg Arg Ala Pro Gln Thr Gly Ile Val Asp Glu Cys Cys
            35                  40                  45

Phe Arg Ser Cys Asp Leu Arg Arg Leu Glu Met Tyr Cys Ala Pro Leu
    50                  55                  60

Lys Pro Ala Lys Ser Ala
65              70

(2) INFORMATION FOR SEQ ID NO:2:

(i) SEQUENCE CHARACTERISTICS:
       (A) LENGTH: 67 amino acids
       (B) TYPE: amino acid
       (D) TOPOLOGY: linear (ii) MOLECULE TYPE: protein (iii) HYPOTHETICAL: NO (ix) FEATURE:
       (A) NAME/KEY: Disulfide-bond
       (B) LOCATION: 9..47
       (D) OTHER INFORMATION: /note= "Disulfide bond between two
           cysteines."

(ix) FEATURE:
       (A) NAME/KEY: Disulfide-bond
       (B) LOCATION: 21..60
       (D) OTHER INFORMATION: /note= "Disulfide bond between two
           cysteines."

(ix) FEATURE:

-continued

```
    (A) NAME/KEY: Disulfide-bond
    (B) LOCATION: 46..51
    (D) OTHER INFORMATION: /note= "Disulfide bond between two
        cysteines."

(xi) SEQUENCE DESCRIPTION: SEQ ID NO:2:

Ala Tyr Arg Pro Ser Glu Thr Leu Cys Gly Gly Glu Leu Val Asp Thr
1               5                   10                  15

Leu Gln Phe Val Cys Gly Asp Arg Gly Phe Tyr Phe Ser Arg Pro Ala
            20                  25                  30

Ser Arg Val Ser Arg Arg Ser Arg Gly Ile Val Glu Glu Cys Cys Phe
        35                  40                  45

Arg Ser Cys Asp Leu Ala Leu Leu Glu Thr Tyr Cys Ala Thr Pro Ala
    50                  55                  60

Lys Ser Glu
65
```